US008323682B2

(12) United States Patent
Cherkassky

(10) Patent No.: US 8,323,682 B2
(45) Date of Patent: Dec. 4, 2012

(54) APPETITE SUPPRESSANT PRODUCT AND METHOD

(76) Inventor: Michael Cherkassky, Fort Worth, TX (US)

( * ) Notice: Subject to any disclaimer, the term of this patent is extended or adjusted under 35 U.S.C. 154(b) by 0 days.

(21) Appl. No.: 13/407,921

(22) Filed: Feb. 29, 2012

(65) Prior Publication Data

US 2012/0157409 A1      Jun. 21, 2012

Related U.S. Application Data

(60) Division of application No. 12/804,471, filed on Jul. 22, 2010, which is a continuation-in-part of application No. 12/218,968, filed on Jul. 21, 2008, now abandoned.

(51) Int. Cl.
*A61K 47/00* (2006.01)

(52) U.S. Cl. ........................................................ 424/439
(58) Field of Classification Search ........................ None
See application file for complete search history.

(56) References Cited

U.S. PATENT DOCUMENTS 3,962,480 A * 6/1976 Wolf et al. ..................... 426/549
4,756,911 A * 7/1988 Drost et al. .................... 424/468

* cited by examiner

*Primary Examiner* — Anand Desai
*Assistant Examiner* — Melissa Mercier
(74) *Attorney, Agent, or Firm* — Lynn E. Barber

(57) ABSTRACT

An appetite suppressant composition that is effective for the control of mammalian weight and methods of administration of the composition of the invention are provided. The composition is a cellulose product prepared with ethanol preferably with added sweetener, spice(s), salt and protein for oral administration to a patient.

5 Claims, No Drawings

APPETITE SUPPRESSANT PRODUCT AND METHOD

CROSS-REFERENCE TO RELATED APPLICATIONS

This application is a divisional application of co-pending U.S. patent application Ser. No. 12/804,471, filed Jul. 22, 2010, which is a continuation-in-part application of co-pending U.S. patent application Ser. No. 12/218,968 filed Jul. 21, 2008.

BACKGROUND OF THE INVENTION

1. Field of the Invention

This invention relates to preparations that assist in weight loss, and in particular relates to preparations and a method for reducing weight by means of appetite suppression.

2. Description of the Related Art

Overweight and obesity are major problems in the western community due to increased consumption and changes in nutritional value of foods that are consumed. Many humans, and their companion animals, suffer from overweight. Today obesity is one of the most serious health problems in the United States, with approximately 30% of adults suffering from obesity, and at least 50% of adults in the United States being overweight. The problem of obesity in the United States and most western countries has been steadily increasing in the last several decades. Such obesity has caused or contributed to a marked increase in the occurrence of heart diseases, hypertension, diabetes, arthritis and increased morbidity and mortality. There is also recent research which links obesity with different types of cancer, particularly breast cancer. Obesity is a serious public health hazard, second in importance only to tobacco. Being overweight reduces lifespan as well as quality of life.

There are many methods suggested for management of obesity and overweight. These include diets that exclude fats and high caloric elements, appetite suppressants, psycho-therapeutic techniques and operative techniques. One of the most common methods is the use of stimulants. Amphetamine-like agents act on the brain to reduce the sensation of hunger. Experience indicates that most of the appetite suppressants work for a short period of time, but a few weeks or a few months later they lose most of their potency and patients start regaining weight. There is also a serious problem with the maintenance of a desirable weight after it is achieved, for the simple reason that appetite suppressants cannot be continued indefinitely at full strength.

The reason that most people become overweight is that they consume more nutrition calories than they require. Also, food is readily available and relatively inexpensive in the developed countries, resulting in inordinate consumption, regulated not only by necessity but also by satisfaction of the palate. In other words, humans do not only eat to survive, but also eat for the taste, flavor and gratification. The degree of the satiety has changed and is predicated not only the necessary nutritional requirements but also on unphysiological "unnatural" pleasure drive.

The complex mechanism that is triggered in the mammalian body during food digestion is characterized by multiple interdependent processes where different hormones with multiple functions influence different organs at the same time, and by that means allow the whole body to function properly.

One of the necessary sensations which completes the mechanism of digestion is satiety. There are many unknown areas in our knowledge of satiety, but the number hormones known to participate in the process of digestion also play a significant role inducing a sense of satiety.

Gastrointestinal peptides are predominantly polypeptides produced in and secreted from specialized gut endocrine cells as well as nerves. The production of gastrointestinal hormones increases when gut endocrine cells are stimulated by food, intraluminal pH, releasing factors, other transmitters or hormones. A number of fairly well-known gastrointestinal hormones are amylin, CCK (cholecystokinin), gastrin, secretin, enterostatin, and neuropeptide Y [3-36]. All of these hormones play their specific role in digestion processes confined to the intestinal tract, and also participate in transmitting information to the brain enabling the brain to be well appraised of the quantity and quality of food being consumed and thus modulating and regulating the amount of food intake from meal to meal. Information from the gastrointestinal tract and oropharynx is newly transmitted to the brain.

It has been proven that hormones reach tractus solitarius via the hypothalamus and concentrating there, they induce satiety, among them CCK, amylin and possibly insulin. Amylin and CCK also reduce gastric emptying and intestinal mobility and thus delay the delivering of food to the intestines and contribute to the early sense of the satiety and as a result limit the overall quantity of food being consumed during a particular meal.

It is therefore an object of the invention to provide a product and a treatment method using certain food ingredients with limited nutritional value but capable of stimulating the intestinal tract to make it possible to reach an early stage of satiety. Such ingredients potentially include but are not limited to pepper, mustard, cinnamon, sugar, sugar substitutes, salt, alcohol, proteins, albumins, and cellulose.

It is a further object of the invention is to provide a composition for effective control of the weight of the mammal to which the composition is administered.

It is a further object of the invention to provide a weight control composition of food products that can act to control the weight of a mammal to which the composition is administered through suppressing the appetite through an early sense of satiety.

It is a further object of the invention to provide methods of administration a composition of food products to control weight without notable side effects.

Other objects and advantages will be more fully apparent from the following disclosure and appended claims.

SUMMARY OF THE INVENTION

The invention herein is a composition effective for the control of mammalian weight and methods of administration of the composition of the invention. The objects of the invention are achieved by administration of a composition comprising a cellulose product prepared with ethanol. Most preferably the composition further comprises sweetener, spice(s), salt and protein. Preferably the composition of the invention is administered orally.

Other objects and features of the inventions will be more fully apparent from the following disclosure and appended claims.

DETAILED DESCRIPTION OF THE INVENTION AND PREFERRED EMBODIMENTS THEREOF

The present invention in its preferred embodiment includes the administration to mammals of a variety of specially combined food ingredients with limited nutritional value which singly or in combination are capable of stimulating intestinal hormones, which in turn influences the brain, specifically the tractus solitarius, and induces early satiety and thus drastically limits the quantity of food consumed at any particular meal. It is also believed that these intestinal hormones also reduce gastric emptying, resulting in the same goal as limiting food consumption.

As used herein, the term "weight loss" includes reduction of weight of a mammal, such as a human being over time. In addition, for persons who have had a pattern of increasing weight over time, the term "weight loss" also can refer to the weight not gained, in other words, the weight benefit of maintaining one's weight as compared to that person's historic/expected weight gain.

Specifically, the preferred single oral dosage consists of a 0.8 cc capsule. The first preferred embodiment does not include caffeine. While the capsule preferably contains a cellulose product (preferably METHOCEL E4M 4000™) which has been mixed with ethanol during the preparation of the capsule, most preferably the capsule also contains a protein product, a spice (e.g., cayenne pepper, mustard), a sweetener (e.g., saccharin), and salt. While capsules are discussed primarily herein, formulations having the same composition and amounts as discussed for the capsule may be prepared for administration as a tablet or other acceptable forms for oral consumption by a patient.

In alternative embodiments of the invention, caffeine is included. The use of caffeine during the weight loss process is that during weight loss, people frequently feel exhausted and tired, and need a boost of energy. While the examples given below use 200 mg caffeine per capsule or 80 mg per capsule, it is understood that these amounts may be varied with a range of physiological acceptable amounts to provide varying stimulant results.

Alternatively, the capsule may be 70% cellulose, 20% proteins, 0.1% pepper, 0.1% saccharin, 0.2% mustard, 2% salt, 0.5% alcohol.

The proportion of ingredients can vary, and additional ingredients may be included.

The composition of the invention is preferably prepared by mixing the ingredients with alcohol to form a paste, and evaporated (e.g., in a drier or microwave). After the evaporation step, only a trace of alcohol (less than 0.5%) at most remains in the product; however, after the treatment with alcohol the product's characteristics are changed, so that the product now has the capability to stimulate neuropeptides, resulting in it being effective as an appetite suppressant. Preferably the paste is put through a mesh to remove large lumps before evaporation. The evaporate product is ground to a fine powder as known in the art, and then dispensed into the final form (capsule, tablet, and the like).

Use of the preparation of the invention that does not contain caffeine is most convenient for night-time use. There are very few appetite suppressants available that do not contain a stimulant, and therefore prior to the invention herein appetite suppressants could not be easily used before sleeping hours, leading to a very large time-gap when the prior appetite suppressants could not be used. Use of the stimulant-free appetite suppressant of the invention can of course be combined with caffeine-containing suppressants used during other times of the day, and thus appetite suppression can be extended to any time of the day and be adapted to a particular patient's needs and schedule.

In addition, the appetite suppressant of the invention herein can be combined with currently commercially available or future preparations without detrimental effect because of the lack of side effects of the invention herein.

Also, the invention herein may be applied using technology and information recognizing a close connection between the tongue, oral cavity, oropharynx and intestines. Thus, when a small tablet is placed in the mouth even without being swallowed, it is known that similar events to satiety are triggered. For this reason, the preferred tablet of the invention also contains various spices, a sweetener such as saccharin, and salts.

The product of the invention herein for most patients is preferably administered in capsule or tablet form. Alternatively, the composition of the invention may be formulated in the form of chewing gum as known in the art and administered to the patient. While the invention herein is discussed primarily with respect to administration to humans, other companion animals that have a tendency to overweight (e.g., cats and dogs) may have the product of the invention administered to them with similar results.

The features of the present invention will be more clearly understood by reference to the following examples, which are not to be construed as limiting the invention.

EXAMPLE 1

Preparation of Composition of the Invention

The composition of the invention is prepared with the following steps:
1—Immerse cellulose product (preferably METHOCEL E4M 4000, Dow Chemical) in alcohol (ethanol)
2—Stir to form a paste so that there is no remaining powdered cellulose product and no free alcohol.
3—Put the paste through a mesh to eliminate large lumps.
4 Evaporate with driers at about 120-130 degrees F.
5—Grind the evaporated product to a fine powder, using methods known in the art.
6—Dispense the fine powder for administration to a client, for example, in a capsule containing 0.8 cc of the powder.

EXAMPLE 2

First Embodiment of Composition of the Invention
(Without Caffeine)

| Category | Substance | Preferred Amount | Range |
|---|---|---|---|
| Cellulose | Methocel E4M 4000 | 7020 cc | 7020 cc |
| Alcohol | Ethanol | 1 gallon | 1 gallon |
| Spice | Pepper | 20 cc | 10-70 cc |
| Salt | NaCl | 20 cc | 15-50 cc |
| Sweetener | Saccharin | 0.5 cc | 0.5-3.0 cc |
| Optional Protein | Whey protein | 300 cc | 150-400 cc |
| Optional | Aluminum chloride | 70 cc | 70-100 cc |
| Optional | Magnesium chloride | 70 cc | 70-100 cc |

The above composition is prepared as discussed in Example 1, and yields about 3990 capsules.

EXAMPLE 3

Second Embodiment of Composition With Caffeine
(200 mg/capsule)

This embodiment has basically the same ingredients as in Example 2 plus caffeine. Preferably, the components of this embodiment as follows:

| Category | Substance | Amount |
|---|---|---|
| Stimulant | Caffeine (anhydrous) | 500 cc |
| | Aluminum chloride | 50 cc |
| | Magnesium chloride | 50 cc |
| Protein | Whey protein | 100 cc |
| Spice | Pepper, cayenne | 300 cc |
| Cellulose | Methocel | 500 cc |
| Composition of Example 2 | Mixed | 300 cc |

EXAMPLE 4

Third Embodiment of the Invention With Reduced Caffeine (80 mg/capsule)

| Category | Substance | Amount |
|---|---|---|
| Stimulant | Caffeine (anhydrous) | 500 cc |
| Spice | Pepper, cayenne | 60 cc |
| Composition of Example 2 | Mixed | 2050 cc |

EXAMPLE 5

Patient Results After Administration of the Invention

Examples of patients to whom capsules according to the invention have been administered for the designated number of months are presented below.

The dosage of the invention for the patients per day are indicated as: RX indicates that the patient was given a standard dose of the indicated prescription appetite suppressant as known in the art, or ½ RX (half standard dose). Phentermine is a standard appetite suppressant used herein in addition to the invention. Typically, for patients over 60-65 years old or if the patient has hypertension, another milder standard appetite suppressant is used, for example, diethylpropion.

In an alternative embodiment of the invention, only an appetite suppressant according to the invention herein is administered to the patient, and a prescription appetite suppressant is not administered, for example when the prescription suppressant to is not necessary or available or when other medical or other considerations as known in the art indicate that a prescription suppressant not be used, for example, the patient's age or condition or preferences.

In addition, once a patient has reached a desired weight, the appetite suppressant according to the invention herein may be administered to the patient for maintenance of the desired weight, or increased amounts may be administered if weight gain occurs.

The abbreviations used below are: W (capsule without caffeine, B (caffeine at 200 mg), Y (caffeine at 80 mg/capsule). In addition to a product according to the invention, the patients also received either phentermine (P) or diethylpropion (D) as part of their treatment (indicated by "RX).

| Patients | Months | Initial Weight | Final Weight | Capsules of Invention* |
|---|---|---|---|---|
| 1 (P) | 9 | 396.4 | 356.4 | 1 RX, B, 2W |
| 2 (P) | 11 | 204.6 | 141.4 | ½ RX, Y, 2W |
| 3 (D) | 6 | 212.0 | 180.8 | RX, W, RX, W |
| 4 (P) | 6 | 443.4 | 312.0 | RX, W, W |
| 5 (D) | 13 | 231.8 | 145.6 | RX, RX-Y, Y |

*Amounts given are per day for a typical administration to that patient.

Depending on the patient's progress (appetite suppression and/or weight change). Patient dosages and type of capsule administered to the patient are changed over the months of treatment as shown, for example, in the next table for a woman patient who was administered phentermine (P) in addition to the capsules of the invention herein.

| Date | Weight | Daily Treatment |
|---|---|---|
| Oct. 14, 2009 | 174.4 | RX (1/4 first 3 days; ½ next 3 days) |
| Nov. 11, 2009 | 165.8 | 6:30-RX; 11:30-Y; 5:00-W |
| Dec. 10, 2009 | 161.4 | 6:30-RX, W; 11:00-Y; 5:30-W |
| Jan. 8, 2010 | 151.4 | 6:30-RX, W; 11:00-Y, W; 5:30-W |
| Feb. 4, 2010 | 146.2 | 6:30-RX, W; 11:00-Y, 2W; 5:30-W |
| Mar. 4, 2010 | 138.8 | 6:30-1/2 RX, W; 11:00-Y, ½W; 5:30-W |
| Apr. 1, 2010 | 139.2 | 6:30-1/4 RX, B; 11:30-B, 2W; 3:30-W; 5:30-W |
| Apr. 29, 2010 | 138.8 | 6:30-1/2 RX, B; 11:00-B, 2W; 3:30-W; 5:50-W |

Thus, if a particular patient reports feeling excessive appetite, additional and/or stronger capsules would be included in the daily regimen for the next time period (e.g., month), while if the patient has reported that the patient's appetite was sufficiently suppressed so that undesirable eating was reduced, the amount of appetite suppressant consumed during the next time period would be maintained or reduced. Similarly, patients who have a need to adjust their caffeine intake in amount or the time of day of intake can have the type of capsule and/or the amount of caffeine-containing capsules adjusted.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method of suppressing appetite in a mammal, comprising mixing a cellulose product, a spice, salt, and a sweetener with alcohol to form a paste, evaporating the alcohol to form an evaporated product, grinding the evaporated product to form a fine powder, dispensing the fine powder to form a product suitable for administration to the mammal, and orally administering the product to the mammal, wherein placing the product in the mouth of the mammal results in appetite suppression in the mammal.

2. The method of suppressing appetite according to claim 1, wherein the cellulose product is METHOCEL E4M 4000™.

3. The method of suppressing appetite according to claim 1, wherein the mammal is a human.

4. A method of forming an appetite suppressant, comprising:
   a) mixing a cellulose product, a spice, salt, and a sweetener with alcohol to form a paste;
   b) evaporated the alcohol from the paste to form an evaporated product;

c) grinding the evaporated product to form a fine powder; and
d) dispensing the fine powder to form a product suitable for oral consumption by a patient, wherein placing the product in the mouth of a mammal results in appetite suppression in the mammal.

5. The method of claim 4, wherein the cellulose product is METHOCEL E4M 4000™.

* * * * *